US012765612B2

(12) United States Patent
Xie et al.

(10) Patent No.: US 12,765,612 B2
(45) Date of Patent: Oct. 20, 2026

(54) BATTERY ASSEMBLY FOR ELECTRONIC VAPORIZATION DEVICE AND ELECTRONIC VAPORIZATION DEVICE

(71) Applicant: Hainan Moore Brothers Technology Co., Ltd., Hainan (CN)

(72) Inventors: Deke Xie, Hainan (CN); Weidong Zhou, Hainan (CN); Zhan Zhao, Hainan (CN); Chao Xu, Hainan (CN); Xiao'an Zhu, Hainan (CN)

(73) Assignee: Hainan Moore Brothers Technology Co., Ltd., Hainan (CN)

( * ) Notice: Subject to any disclaimer, the term of this patent is extended or adjusted under 35 U.S.C. 154(b) by 734 days.

(21) Appl. No.: 18/318,199

(22) Filed: May 16, 2023

(65) Prior Publication Data

US 2023/0371613 A1 Nov. 23, 2023

(30) Foreign Application Priority Data

May 19, 2022 (CN) ......................... 202221205415.9

(51) Int. Cl.

| | |
|---|---|
| ***A24F 40/60*** | (2020.01) |
| ***A24F 40/40*** | (2020.01) |
| ***A24F 40/50*** | (2020.01) |
| ***F21V 8/00*** | (2006.01) |
| ***H01M 50/202*** | (2021.01) |
| ***H01M 50/262*** | (2021.01) |
| ***H01M 50/284*** | (2021.01) |
| ***H05K 1/14*** | (2006.01) |
| *A61M 15/06* | (2006.01) |

(52) U.S. Cl.

CPC .............. *A24F 40/60* (2020.01); *A24F 40/40* (2020.01); *A24F 40/50* (2020.01); *G02B 6/0068* (2013.01); *G02B 6/0091* (2013.01); *H01M 50/202* (2021.01); *H01M 50/262* (2021.01); *H01M 50/284* (2021.01); *H05K 1/144* (2013.01); *A61M 15/06* (2013.01); *H01M 2220/30* (2013.01); *H05K 2201/048* (2013.01)

(58) Field of Classification Search

CPC ........... A24F 40/60; A24F 40/40; A24F 40/50

See application file for complete search history.

(56) References Cited

FOREIGN PATENT DOCUMENTS

| | | | |
|---|---|---|---|
| CN | 215913309 | U | 3/2022 |
| CN | 216019130 | U | 3/2022 |
| CN | 218041920 | U | 12/2022 |
| CN | 115568086 | A | 1/2023 |

(Continued)

OTHER PUBLICATIONS

Office Action issued in corresponding GB Patent Application No. 2307550.0, dated Nov. 20, 2023.

*Primary Examiner* — Robert Grant

(74) *Attorney, Agent, or Firm* — Leydig, Voit & Mayer, Ltd.

(57) ABSTRACT

A battery assembly for an electronic vaporization device includes: a first circuit board for controlling operation of the electronic vaporization device; a second circuit board, stacked with the first circuit board, an orthographic projection of the second circuit board on the first circuit board not exceeding a maximum distance of the first circuit board in a length direction or a width direction; and a plurality of light emitting elements arranged on a surface of the second circuit board away from the first circuit board.

8 Claims, 4 Drawing Sheets

(56) References Cited

FOREIGN PATENT DOCUMENTS

| | | | | | |
|---|---|---|---|---|---|
| CN | 218418413 | U | | 2/2023 | |
| CN | 218999527 | U | | 5/2023 | |
| WO | WO-2016165063 | A1 | * | 10/2016 | ............ A24F 40/95 |
| WO | 2022175133 | A1 | | 8/2022 | |

* cited by examiner

BATTERY ASSEMBLY FOR ELECTRONIC VAPORIZATION DEVICE AND ELECTRONIC VAPORIZATION DEVICE

CROSS-REFERENCE TO PRIOR APPLICATION

Priority is claimed to Chinese Patent Application No. 202221205415.9, filed on May 19, 2022, the entire disclosure of which is hereby incorporated by reference herein.

FIELD

The present invention relates to the technical field of vaporization devices, and in particular, to a battery assembly for an electronic vaporization device and an electronic vaporization device.

BACKGROUND

The electronic vaporization device has become a relatively mature product on the market. It vaporizes a vaporizing medium through a vaporizer to generate smoke, and the user inhales the smoke to obtain effective substances in the e-liquid. The electronic vaporization device is mainly composed of a vaporizer and a battery assembly. The battery assembly is generally equipped with a light emitting unit, configured to indicate a battery level and control of the electronic vaporization device. The battery assembly in the conventional electronic vaporization device has a large volume, and takes up a lot of space. How to reduce the space occupied by the battery assembly is an urgent problem to be resolved.

SUMMARY

In an embodiment, the present invention provides a battery assembly for an electronic vaporization device, comprising: a first circuit board configured to control operation of the electronic vaporization device; a second circuit board, stacked with the first circuit board, an orthographic projection of the second circuit board on the first circuit board not exceeding a maximum distance of the first circuit board in a length direction or a width direction; and a plurality of light emitting elements arranged on a surface of the second circuit board away from the first circuit board.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
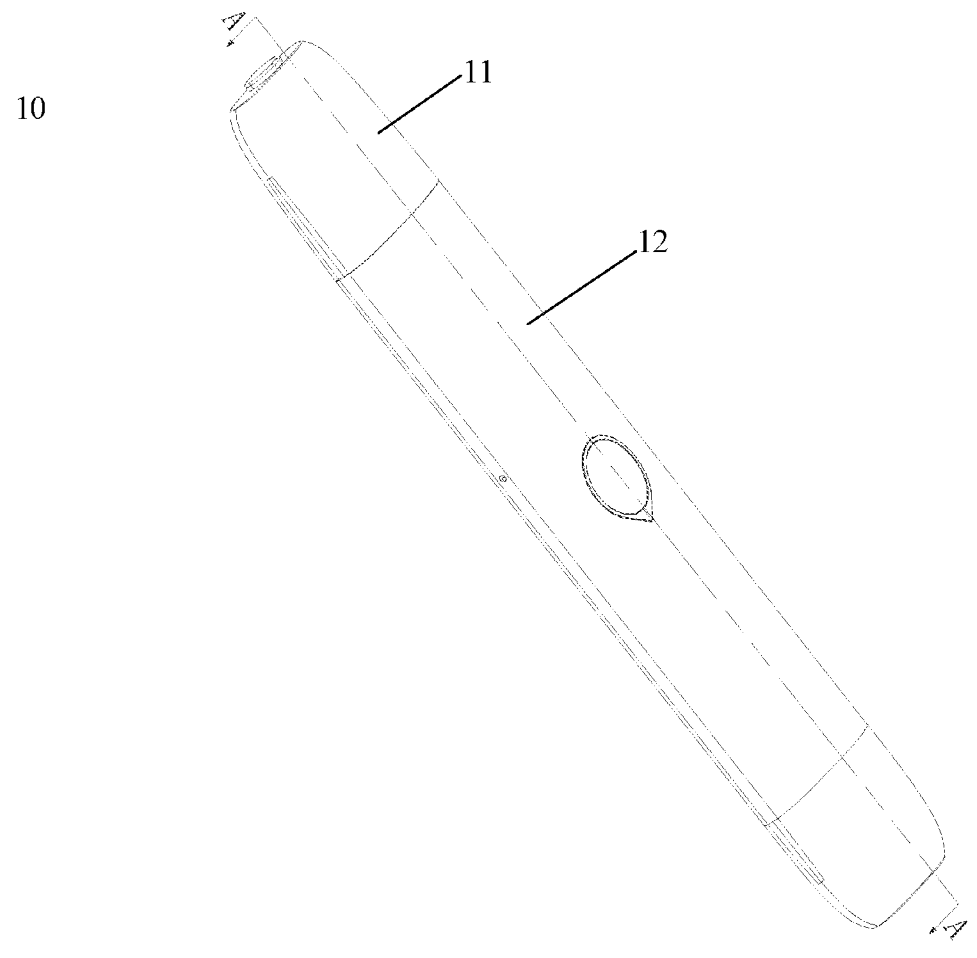
FIG. 1 is a schematic structural diagram of an electronic vaporization device according to an embodiment.

In an embodiment, the present invention provides a battery assembly for an electronic vaporization device and an electronic vaporization device, to reduce space occupied by the battery assembly.

A battery assembly for an electronic vaporization device includes:

- a first circuit board, configured to control operation of the electronic vaporization device;
- a second circuit board, stacked with the first circuit board, where an orthographic projection of the second circuit board on the first circuit board does not exceed a maximum distance of the first circuit board in a length direction or a width direction; and
- a plurality of light emitting elements, arranged on a surface of the second circuit board away from the first circuit board.

In one of the embodiments, the second circuit board further includes a touch element, and the touch element is arranged on a side of the second circuit board away from the first circuit board and is configured to sense a touch operation.

In one of the embodiments, the plurality of light emitting elements are arranged at intervals around the touch element, and the plurality of light emitting elements light up in response to the touch operation sensed by the touch element.

In one of the embodiments, the battery assembly further includes a light guide element, and the light guide element is arranged on a side of the second circuit board away from the first circuit board, covers the light emitting elements, and is configured to transmit light of the light emitting elements.

In one of the embodiments, the light guide element includes a light guide support and a light guide sheet; the light emitting element, the light guide support, and the light guide sheet are stacked in sequence, the light guide sheet is connected to a shell of the battery assembly, and the light is refracted by the light guide support and the light guide sheet achieve double-layer light guiding.

In one of the embodiments, the light guide support comprises a first light guide portion and a second light guide portion, an end of the first light guide portion is supported on the side of the second circuit board away from the first circuit board, and the second light guide portion is connected to the first light guide portion and located above the light emitting element; and the other end of the first light guide portion away from the second circuit board and the second light guide portion define an accommodating cavity configured to accommodate the light guide sheet.

In one of the embodiments, a side of the light guide sheet away from the light guide support is provided with a touch cavity, the touch element is accommodated in the touch cavity, and a touch end of the touch element extends out of the touch cavity to be in touch connection with the second circuit board.

In one of the embodiments, at least one of space between the light guide support and the light guide sheet and space between the light guide sheet and the touch element is filled with a waterproof layer.

In one of the embodiments, the battery assembly further includes a battery holder and a fastener, an area of the second circuit board is smaller than that of the first circuit board, and the first circuit board is further provided with a positioning hole in a region outside the orthographic projection of the second circuit board, where the fastener passes through the positioning hole and is fixedly connected to the battery holder.

An electronic vaporization device includes the foregoing battery assembly.

In the battery assembly for an electronic vaporization device and the electronic vaporization device, the second circuit board and the first circuit board are stacked, the orthographic projection of the second circuit board on the first circuit board does not exceed the maximum distance of the first circuit board in the length direction or width direction, and the light emitting elements are arranged on the surface of the second circuit board away from the first circuit board, which effectively reduces space occupied by the battery assembly.

REFERENCE NUMERALS

10. electronic vaporization device; 11. vaporizer; 12. battery assembly; 110. first circuit board; 120. microphone; 130. positioning screw; 210. second circuit board; 220. light emitting element; 230. touch element; 242. light guide support; 2422. first light guide portion; 2424. second light guide portion; 2426. accommodating cavity; 244. light guide sheet; 2442. touch cavity; 250. waterproof layer.

To make the objectives, technical solutions, and advantages of the present invention clearer and more understandable, the present invention is further described in detail below with reference to accompanying drawings and embodiments. It is to be understood that the specific embodiments described herein are only used for explaining the present invention, and are not used for limiting the present invention.

Unless otherwise defined, meanings of all technical and scientific terms used in this specification are the same as those usually understood by a person skilled in the art to which the present invention belongs. In this specification, terms used in the specification of the present invention are merely intended to describe objectives of the specific embodiments, but are not intended to limit the present invention.

It will be understood that "connected" in the following embodiments is to be interpreted as "electrically connected", "communicatively connected", etc. if electrical signals or data is transferred between the connected circuits, modules, units, etc.

As shown in FIG. 1, this embodiment provides an electronic vaporization device 10, which can be configured to vaporize a liquid substrate. The electronic vaporization device 10 includes a vaporizer 11 and a battery assembly 12. An end of the vaporizer 11 is detachably connected to the battery assembly 12. When the vaporizer 11 needs to be replaced, the vaporizer 11 can be detached from the battery assembly 12, and a new vaporizer 11 is connected to the battery assembly 12, to realize reuse of the battery assembly 12.

The vaporizer 11 may be used in different fields such as medical vaporization, electronic vaporization, etc. The vaporizer 11 is configured to store a to-be-vaporized substrate and vaporize the to-be-vaporized substrate to generate an aerosol. In this embodiment, the vaporizer 11 is configured to vaporize the to-be-vaporized substrate to generate the aerosol to be inhaled by a user. Certainly, in other embodiments, the vaporizer 11 may also be applied to hair spray equipment to vaporize hair spray for hair fixing. Alternatively, the vaporizer is applied to medical equipment for treating diseases of upper and lower respiratory systems to vaporize medical drugs. The battery assembly 12 is configured to supply power to the vaporizer 11, to enable the vaporizer 11 to vaporize the liquid substrate to generate the aerosol.

The vaporizer 11 includes a first shell, a mounting base, and a vaporization core. A liquid storage cavity, a mounting cavity, and an air outlet channel are formed in the first shell. The liquid storage cavity is configured to store the to-be-vaporized liquid substrate. The liquid storage cavity may be made of aluminum, stainless steel, or other metals, or made of plastic, provided that the liquid storage cavity can store the to-be-vaporized liquid substrate and does not react with the stored liquid substrate to cause deterioration. A shape and size of the liquid storage cavity are not limited, which may be designed as required.

The first shell forms a mounting cavity on a side of the liquid storage cavity close to the battery assembly 12. The air outlet channel and the liquid storage cavity are arranged side by side on a same side of the mounting cavity, and the air outlet channel communicates with the external atmosphere. The mounting base is arranged on a side of the mounting cavity close to the battery assembly 12. The vaporization core is mounted on the mounting base, and engaged with the mounting base to form a vaporization cavity. The vaporization cavity communicates with the air outlet channel, that is, the vaporization cavity, the air outlet channel, and the external atmosphere communicate with each other. An end of the mounting base close to the battery assembly 12 is exposed, and the mounting base is detachably connected to the first shell.

The vaporization core is configured to vaporize the to-be-vaporized substrate in the liquid storage cavity to generate the aerosol. The vaporization core includes a heating element and a porous element. The liquid in the liquid storage tank enters the porous element. The porous element guides the to-be-vaporized liquid substrate to the heating element by capillary force. The heating element heats and vaporizes the liquid substrate to generate the aerosol. The heating element may be a heating wire, a heating mesh, a heating film, a heating circuit, etc., which can be selected as needed. The porous element may be a porous ceramic or a cotton core.

The battery assembly 12 includes a second shell, a first circuit board, a light emitting unit, and a battery. The light emitting unit includes a second circuit board and a plurality of light emitting elements. The second shell is provided with an accommodating cavity. The battery is arranged in the accommodating cavity, and is configured to supply power to the vaporization core.

Figure 2:
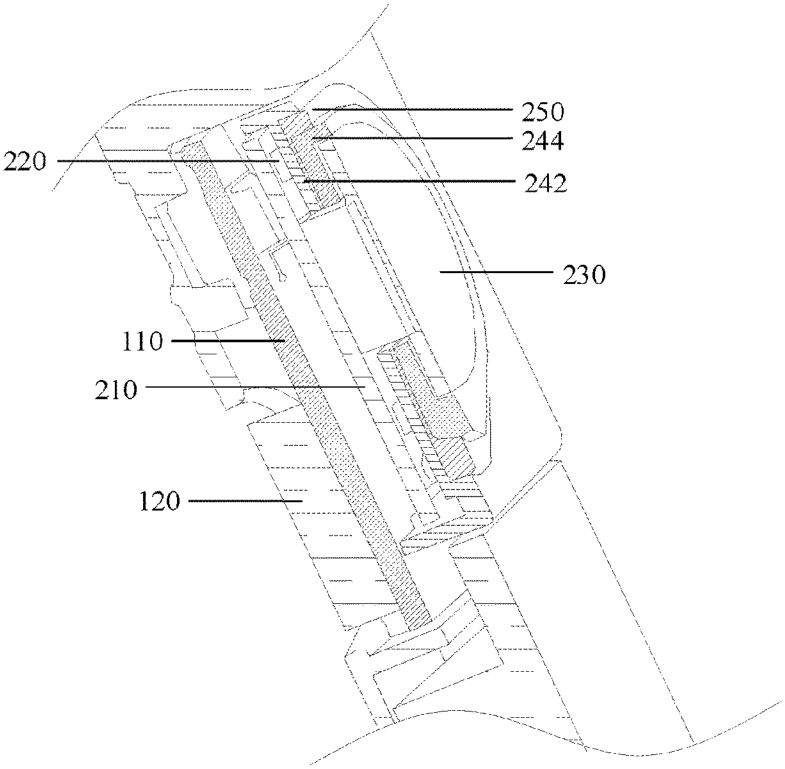
FIG. 2 is a schematic diagram of a cross-sectional structure of the electronic vaporization device in FIG. 1 taken along A-A according to an embodiment.
Figure 3:
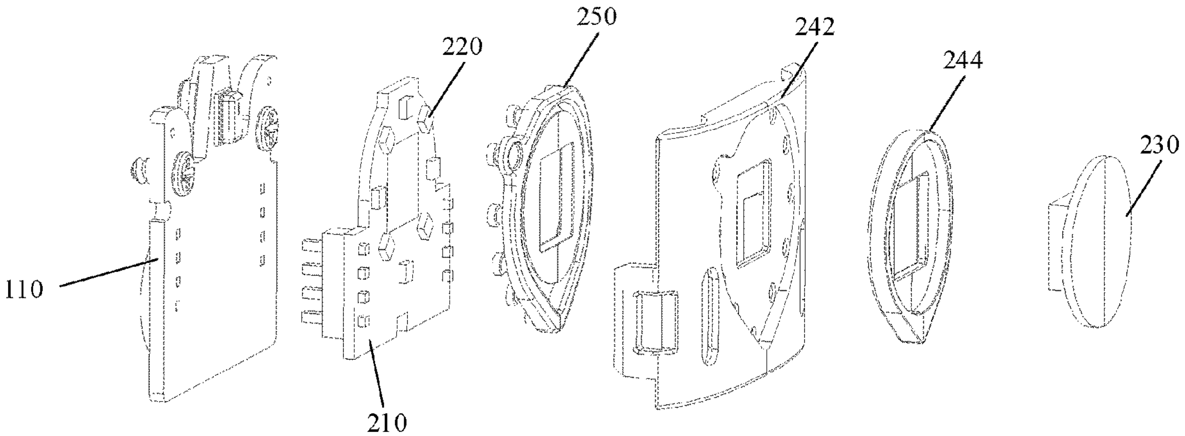
FIG. 3 is an exploded schematic diagram of a battery assembly according to an embodiment.

In an embodiment, as shown in FIG. 2 and FIG. 3, a battery assembly for an electronic vaporization device is provided. The battery assembly includes a first circuit board 110, a second circuit board 210, and a plurality of light emitting elements 220. The first circuit board 110 is configured to control operation of the electronic vaporization device. The second circuit board 210 is stacked with the first circuit board 110, and an orthographic projection of the second circuit board 210 on the first circuit board 110 does not exceed a maximum distance of the first circuit board 110 in a length direction or width direction. The plurality of light emitting elements 220 are arranged on a surface of the second circuit board 210 away from the first circuit board 110.

Specifically, the first circuit board 110 is provided with solder joints. The second circuit board 210 is stacked with the first circuit board 110 and fixed with the solder joints, and performs data transmission with the first circuit board 110 through the solder joints. A side of the first circuit board 110 facing away from the second circuit board 210 is used for arranging components, which may include a microphone 120 and other components. A side of the first circuit board 110 facing the second circuit board 210 is provided with traces. The traces are connected to the components on the first circuit board 110, and perform data transmission with the second circuit board 210 through the solder joints. The first circuit board 110 can be substantially rectangular, and has jagged long sides or width sides due to installation requirements, while the orthographic projection of the second circuit board 210 on the first circuit board 110 does not exceed the maximum distance of the first circuit board 110 in the length direction or width direction, to reduce overall space occupied by the second circuit board 210 and the first circuit board 110 in the battery assembly. A side of the second circuit board 210 facing away from the first circuit board 110 is provided with a plurality of light emitting elements 220, and a side of the second circuit board 210 facing the first circuit board 110 can be provided with related functional devices. The light emitting element 220 is not limited to a unique type, but may be a light-emitting diode (LED) lamp, or other types of light-emitting lamps.

In an embodiment, as shown in FIG. 2 and FIG. 3, the second circuit board 210 further includes a touch element 230. The touch element 230 is arranged on a side of the second circuit board 210 away from the first circuit board 110 to sense a touch operation. Further, the plurality of light emitting elements 220 are arranged at intervals around the touch element 230. The plurality of light emitting elements 220 light up in response to the touch operation sensed by the touch element 230.

A touch region may be arranged on a shell of the electronic vaporization device, and the touch region is flush with the shell. An electrical signal is generated upon a finger touch by a user, and the touch element 230 on the second circuit board 210 responds to the touch operation. The user can perform a corresponding touch operation on the touch region of the electronic vaporization device. The second circuit board 210 generates an instruction according to the touch operation sensed by the touch element 230 and transmits the instruction to the first circuit board 110. The first circuit board 110 performs a corresponding control function according to the instruction, for example, controlling the electronic vaporization device to turn on or turn off, adjusting parameters, and turning on or off of the light emitting elements 220. For example, after the user starts the electronic vaporization device, the first circuit board 110 transmits a control signal to the second circuit board 210 to control the light emitting elements 220 to light up, flash, or emit gradually changing light. The first circuit board 110 then adjusts parameters of the device with reference to the touch operation of the user, for example, adjusting a vaporization power level. In addition, after the user performs a shutdown touch operation, the first circuit board 110 transmits a control signal to the second circuit board 210 to control the light emitting elements 220 to turn off, and control the device to shut down.

In the battery assembly for an electronic vaporization device, the second circuit board 210 and the first circuit board 110 are stacked, the orthographic projection of the second circuit board 210 on the first circuit board 110 does not exceed the maximum distance of the first circuit board 110 in the length direction or width direction, and the light emitting elements 220 are arranged on the surface of the second circuit board 210 away from the first circuit board 110, which effectively reduces space occupied by the battery assembly.

Figure 4:
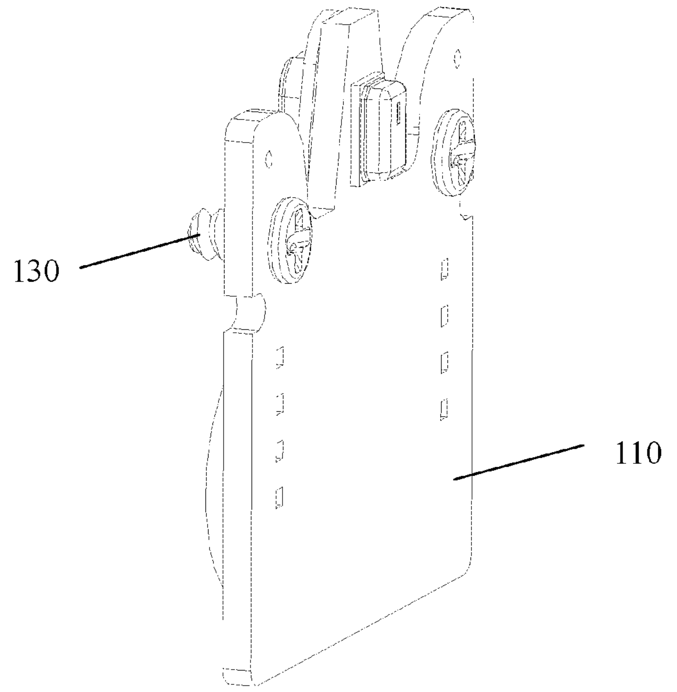
FIG. 4 is a schematic structural diagram of a first circuit board of a battery assembly according to an embodiment.

In an embodiment, the battery assembly further includes a battery holder and a fastener. An area of the second circuit board 210 is smaller than that of the first circuit board 110, and a region of the first circuit board 110 outside the orthographic projection of the second circuit board 210 is provided with a positioning hole. As shown in FIG. 4, the fastener passes through the positioning hole and is fixedly connected to the battery holder. Specifically, the fastener may be a positioning screw 130 or other components capable of fixing the battery holder and the first circuit board 110. The area of the second circuit board 210 is designed to be smaller than that of the first circuit board 110, that is, the orthographic projection of the second circuit board 210 on the first circuit board 110 only covers a partial region of the first circuit board 110. The positioning hole is designed in a region of the first circuit board 110 not covered by the orthographic projection of the second circuit board 210, which facilitates engagement between the positioning hole and the positioning screw, so that the first circuit board 110 can be fixedly connected to the battery holder. Further, thicknesses of the second circuit board 210 and the first circuit board 110 can be designed according to actual requirements. In this embodiment, the thicknesses of the second circuit board 210 and the first circuit board 110 can be designed within a range of 0.7 mm to 1 mm, and a total thickness from the second circuit board 210 to the first circuit board 110 can be designed within a range of 2.5 mm to 3.5 mm.

In an embodiment, the light emitting unit of the battery assembly further includes a light guide element. The light guide element is arranged on the side of the second circuit board 210 away from the first circuit board 110. The light guide element covers the light emitting elements 220, to transmit light of the light emitting elements 220. By arranging the light guide element on the second circuit board 210, the light is guided when the light emitting elements 220 are turned on, to improve uniformity of light emission. Further, the light guide element is not limited to a unique structure, but may be a single-layer structure or a multi-layer structure. In an embodiment, as shown in FIG. 2 and FIG. 3, the light guide element includes a light guide support 242 and a light guide sheet 244. The light emitting element 220, the light guide support 242, and light guide sheet 244 are stacked in sequence. The light guide sheet 244 is connected to a shell of the battery assembly, and light is refracted by the light guide support 242 and the light guide sheet 244 to achieve double-layer light guiding. A refraction direction of the light is changed by arranging two components: the light guide support 242 and the light guide sheet 244, to achieve the double-layer light guiding, thereby further achieving a uniform luminescence effect.

Figure 5:
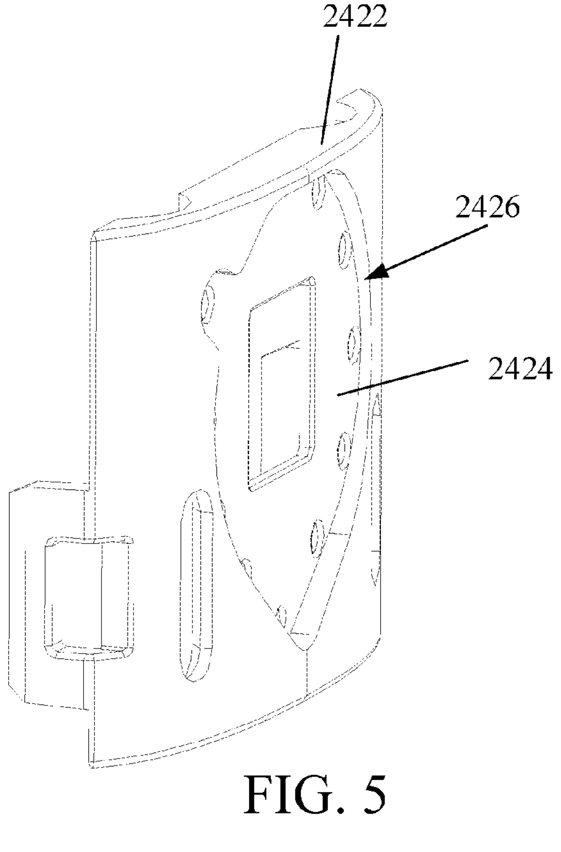
FIG. 5 is a schematic structural diagram of a light guide support of a battery assembly according to an embodiment.

Specific structures of the light guide support 242 and the light guide sheet 244 are not unique. In one embodiment, as shown in FIG. 5, the light guide support 242 includes a first light guide portion 2422 and a second light guide portion 2424. One end of the first light guide portion 2422 is supported on a side of the second circuit board 210 away from the first circuit board 110, and the second light guide portion 2424 is connected to the first light guide portion 2422 and located above the light emitting element 220. The other end of the first light guide portion 2422 away from the second circuit board 210 and the second light guide portion 2424 define an accommodating cavity 2426 configured to accommodate the light guide sheet 244. The second light guide portion 2424 is fixed by the first light guide portion 2422, so that a gap is formed between the second light guide portion 2424 and the second circuit board 210, to arrange the light emitting element 220. The first light guide portion 2422 and the second light guide portion 2424 form an accommodating cavity 2426 to accommodate the light guide sheet 244, which facilitates transmission of light between the light guide support 242 and the light guide sheet 244, and further reduces the space occupied by the battery assembly.

Figure 6:
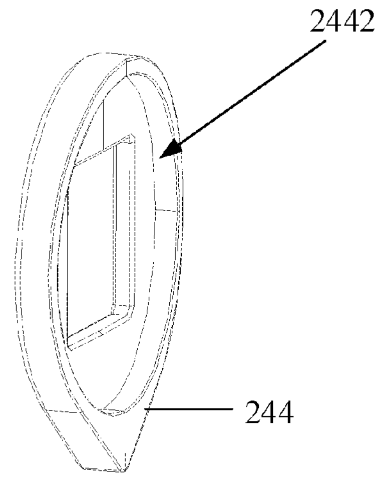
FIG. 6 is a schematic structural diagram of a light guide sheet of a battery assembly according to an embodiment.

Further, as shown in FIG. 6, in an embodiment, a side of the light guide sheet 244 away from the light guide support 242 is provided with a touch cavity 2442. The touch element 230 is accommodated in the touch cavity 2442, and a touch end of the touch element 230 extends out of the touch cavity and is connected to the second circuit board 210. A sensing end of the touch element 230 is located in the touch cavity 2442, to form a touch region exposed from the shell. The touch region is configured to sense the touch operation of the user on the shell of the electronic vaporization device. The touch end of the touch element 230 is connected to the second circuit board 210, and transmits sensing data to the second circuit board 210. Specifically, the light guide sheet 244 and the second light guide portion 2424 may be each provided with a via hole, such that the touch end of the touch element is connected to the second circuit board 210 through the via holes after the touch element 230 is arranged in the touch cavity 2442 of the light guide sheet 244. Alternatively, the light guide sheet 244 and first light guide portion 2422 may be each provided with a via hole, such that the touch end of the touch element 230 is connected to the second circuit board 210 through the via holes. The touch end and the sensing end of the touch element 230 can be connected by a conductive foam or a flexible circuit. In this embodiment, the touch element 230 is accommodated in the touch cavity 2442 of the light guide sheet 244, which can also reduce the space occupied by the battery assembly.

In addition, as shown in FIG. 3, the touch element 230 can be designed to be circular, the light emitting element 220 can be arranged in a circle around the touch element 230, and a distance from the light emitting element 220 to the shell of the electronic vaporization device can be designed to be 1.9 mm.

Figure 7:
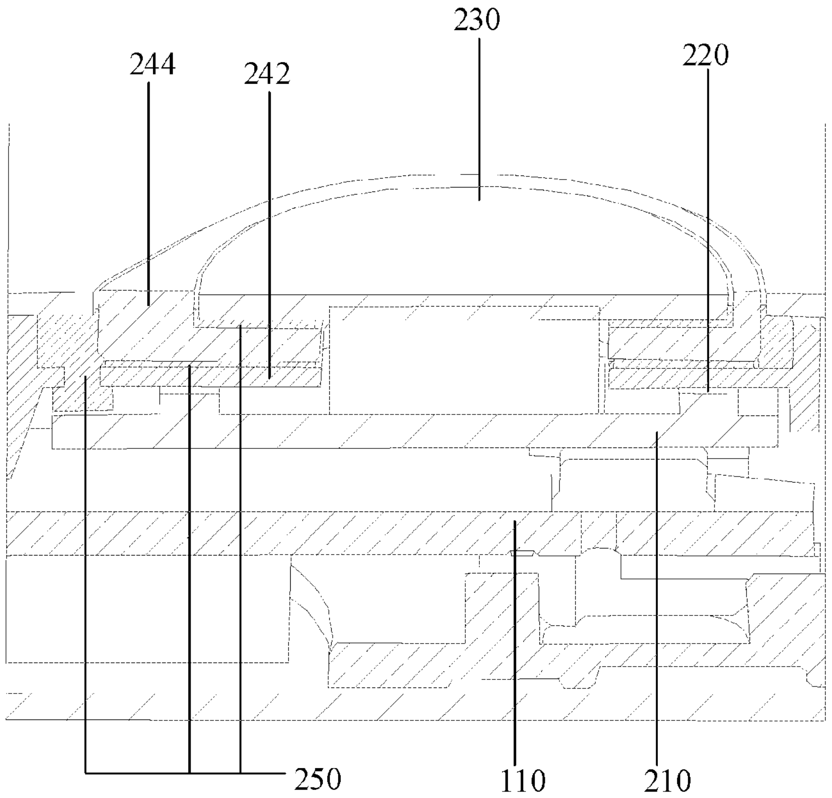
FIG. 7 is a schematic diagram of a cross-sectional structure of the electronic vaporization device in FIG. 1 taken along A-A according to another embodiment.

In an embodiment, as shown in FIG. 3 and FIG. 7, the battery assembly further includes a waterproof layer 250. At least one of space between the light guide support 242 and the light guide sheet 244 and space between the light guide sheet 244 and the touch element 230 is filled with the waterproof layer 250. Specifically, the waterproof layer 250 may be arranged only between the light guide support 242 and the light guide sheet 244, or the waterproof layer 250 may be arranged only between the light guide sheet 244 and the touch element 230, or the waterproof layer 250 may be arranged at both positions. The waterproof layer 250 may be specifically a filling layer made of a flexible material. an assembly gap between the light guide support 242 and the light guide sheet 244 or an assembly gap between the light guide sheet 244 and the touch element 230 is filled with the waterproof layer 250, to reduce a risk of foreign matter entering the gap.

In an embodiment, an electronic vaporization device is further provided, including the foregoing battery assembly.

In the battery assembly of the electronic vaporization device, the second circuit board 210 and the first circuit board 110 are stacked, the orthographic projection of the second circuit board 210 on the first circuit board 110 does not exceed the maximum distance of the first circuit board 110 in the length direction or width direction, and the light emitting elements 220 are arranged on the surface of the second circuit board 210 away from the first circuit board 110, which effectively reduces space occupied by the battery assembly.

In order to facilitate a better understanding of the foregoing electronic vaporization device, the battery assembly, and the light guide plate thereof, a detailed description is provided below with reference to the specific embodiments.

At present, thinning and lightening is an important development trend of the electronic vaporization device. In a process of thinning and lightening, a thinning and lightening design of the battery assembly is an important technical problem to be resolved. Based on this, the present invention provides a circuit structure of the light guide plate in the battery assembly. Double-layer circuit boards are stacked in a thickness direction to save space, and the double-layer light guide structure is adopted to achieve an effect of uniform luminescence. A visual effect of flashing touch buttons and LED lamps is realized in a small space through the stacking design, and the structure is reliable.

Specifically, as shown in FIG. 2 to FIG. 7, the battery assembly includes a first circuit board 110, a second circuit board 210, a light emitting element 220, a touch element 230, a light guide element, and a waterproof layer 250. The light emitting element 220 is an LED lamp, and the second circuit board 210 is an LED lamp plate. The first circuit board 110 and the LED lamp plate are stacked in a thickness direction. A plurality of components, including a microphone 120 and other components, are arranged on a side of the first circuit board 110 facing away from the LED lamp plate, and traces are arranged on a side of the first circuit board 110 facing the LED lamp plate. An LED lamp and a touch element 230 are arranged on a side of the LED lamp plate facing away from the first circuit board 110, and related functional devices are arranged on a side of the LED lamp plat facing the first circuit board 110.

In an orthographic projection direction along the thickness, an area of the LED lamp plate is smaller than that of the first circuit board 110. A positioning hole of the first circuit board 110 is exposed, and is configured to engage with the positioning screw 130, for the first circuit board 110 to be fixedly connected to the battery holder. The first circuit board 110 and the LED lamp plate are connected through solder joints. The solder joints are used for fixing a position of the LED lamp plate, and serving as data transmission points for the first circuit board 110 to control the LED lamp plate. A total thickness of the LED lamp plate and the first circuit board 110 ranges from 2.5 mm to 3.5 mm (except outermost components). The LED lamp plate and the first circuit board 110 each have a thickness approximately ranging from 0.7 mm to 1 mm, and a size of the first circuit board 110 is 16 mm*16 mm.

A touch element 230 is arranged in the middle of the LED lamp plate, and a circle of LED lamps are arranged around the touch element 230. The following program is written in advance: in response to a key operation on the touch element 230, the electronic vaporization device is started (other functions can also be realized), and at the same time, the LED lamps light up, flash, or breath in a gradient manner. The first circuit board 110 is designed with a jagged structure, with a silicon microphone in the middle, serving as a start switch of the microphone 120; two digging grooves are provided nearby to avoid strokes of solder joints and a spring needle, and an outermost side of the first circuit board 110 is provided with positioning holes. On the LED lamp plate, components in a touch function region are designed in a direction towards the first circuit board 110, and are not in direct contact with the first circuit board 110. Data transmission is realized through six solder joints.

Since the light source (that is, the LED lamps) is relatively close to an appearance display surface (specifically at a distance of 1.9 mm), bright spots and uneven light emission easily occur. Therefore, the present invention adopts a double-layer light guide structure, to change a refraction direction though two components: the light guide support 242 and the light guide sheet 244, to implement double-layer light guiding, thereby achieving the effect of uniform luminescence. In addition, due to the risk of foreign matter entering the assembly gaps of the touch element 230, in this solution, a waterproof layer 250 is formed by adding a flexible material between the light guide support 242 and the light guide sheet 244, and between the light guide sheet 244 and the touch element 230 to fill up the assembly gaps to achieve a protection purpose.

In the circuit structure of the light guide plate in the battery assembly, double-layer circuit boards are stacked in the thickness direction to save space; the double-layer light guide structure is adopted to achieve the effect of uniform luminescence, and the waterproof layer 250 is used, to avoid the risk of foreign matter entering the assembly gaps of the touch keys. A visual effect of flashing touch buttons and LED lamps is realized in a small space through the stacking design, and the structure is reliable.

The technical features in the foregoing embodiments may be randomly combined. For concise description, not all possible combinations of the technical features in the embodiments are described. However, provided that combinations of the technical features do not conflict with each other, the combinations of the technical features are considered as falling within the scope described in this specification.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A battery assembly for an electronic vaporization device, comprising:

a first circuit board configured to control operation of the electronic vaporization device;

a second circuit board, stacked with the first circuit board, an orthographic projection of the second circuit board on the first circuit board not exceeding a maximum distance of the first circuit board in a length direction or a width direction;

a touch element arranged on a side of the second circuit board away from the first circuit board and configured to sense a touch operation; and a plurality of light emitting elements arranged on the side of the second circuit board away from the first circuit board at intervals around the touch element, the plurality of light emitting elements configured to light up in response to the touch operation sensed by the touch element.

2. The battery assembly of claim 1, further comprising:

a light guide element arranged on the side of the second circuit board away from the first circuit board, the light guide element covering the plurality of light emitting elements and being configured to transmit light of the plurality of light emitting elements.

3. The battery assembly of claim 2, wherein the light guide element comprises a light guide support and a light guide sheet, wherein the light emitting element, the light guide support, and the light guide sheet are stacked in sequence, the light guide sheet is connected to a shell of the battery assembly, and light is refracted by the light guide support and the light guide sheet to achieve double-layer light guiding.

4. The battery assembly of claim 3, wherein the light guide support comprises a first light guide portion and a second light guide portion, an end of the first light guide portion is supported on a side of the second circuit board away from the first circuit board, and the second light guide portion is connected to the first light guide portion and located above the light emitting element, and wherein another end of the first light guide portion away from the second circuit board and the second light guide portion define an accommodating cavity configured to accommodate the light guide sheet.

5. The battery assembly of claim 4, wherein a side of the light guide sheet away from the light guide support comprises a touch cavity, the touch element being accommodated in the touch cavity, and a touch end of the touch element extending out of the touch cavity to be in touch connection with the second circuit board.

6. The battery assembly of claim 3, wherein at least one of space between the light guide support and the light guide sheet and space between the light guide sheet and the touch element is filled with a waterproof layer.

7. The battery assembly of claim 1, further comprising:

a battery holder; and a fastener, wherein an area of the second circuit board is smaller than an area of the first circuit board, wherein the first circuit board comprises a positioning hole in a region outside the orthographic projection of the second circuit board, and wherein the fastener passes through the positioning hole and is fixed to the battery holder.

8. An electronic vaporization device, comprising:

the battery assembly of claim 1.

* * * * *